United States Patent [19]

Garver, Sr. et al.

[11] Patent Number: 4,508,534

[45] Date of Patent: Apr. 2, 1985

[54] ASSEMBLY EMPLOYING A BREAKABLE THERMAL BOND WHICH IS NOT SUBSTANTIALLY EFFECTED BY PROLONGED HEAT EXPOSURE

[75] Inventors: Edward B. Garver, Sr., Lindenhurst; Kenneth D. Zabielski, McHenry, both of Ill.

[73] Assignee: Baxter Travenol Laboratories, Inc., Deerfield, Ill.

[21] Appl. No.: 495,281

[22] Filed: May 16, 1983

Related U.S. Application Data

[63] Continuation of Ser. No. 326,737, Dec. 2, 1981, Pat. No. 4,402,682.

[51] Int. Cl.$^3$ .............................................. A61M 5/32
[52] U.S. Cl. ................................. 604/111; 604/263; 604/272
[58] Field of Search ............... 604/111, 263, 272, 283, 604/905, 192, 198; 260/42.49, 29.1 SB; 525/100, 104, 101, 105, 106

[56] References Cited

U.S. PATENT DOCUMENTS

| | | | |
|---|---|---|---|
| 3,428,707 | 2/1969 | Amos et al. | 260/42.49 |
| 3,687,890 | 8/1972 | Susuki et al. | |
| 3,959,192 | 5/1976 | Delfosse et al. | 260/42.49 |
| 3,966,673 | 6/1976 | Frick et al. | |
| 4,032,494 | 6/1977 | Gentry | |
| 4,035,453 | 7/1977 | Hittman et al. | 260/29.1 SB |
| 4,177,182 | 12/1979 | Ichikawa et al. | 260/29.1 SB |
| 4,231,909 | 11/1980 | Fearon et al. | |
| 4,289,859 | 9/1981 | Kalinowski et al. | 260/29.1 SB |

*Primary Examiner*—C. Fred Rosenbaum
*Assistant Examiner*—Michelle N. Lester
*Attorney, Agent, or Firm*—Paul C. Flattery; Daniel D. Ryan

[57] ABSTRACT

An assembly for supporting a cannula comprises a hub which supports the cannula and which includes a post portion which concentrically surrounds a section of the cannula adjacent to the hub. The assembly also includes a cover which is attachable to the post portion of the hub to enclose the cannula. The cover and post portion are coupled together by a "tamper-proof" connection which normally resists removal of the cover, and thereby attests to the sterile integrity of the needle. The connection can be broken in response to the deliberate application of a predetermined rotational force by the user upon the cover and cannot thereafter be recreated, thereby serving as an outward indication that the sterile integrity of the cannula has been compromised. Both the post portion and the cover remain physically intact, despite the breakage of the connection, to permit return of the cover when desired.

1 Claim, 13 Drawing Figures

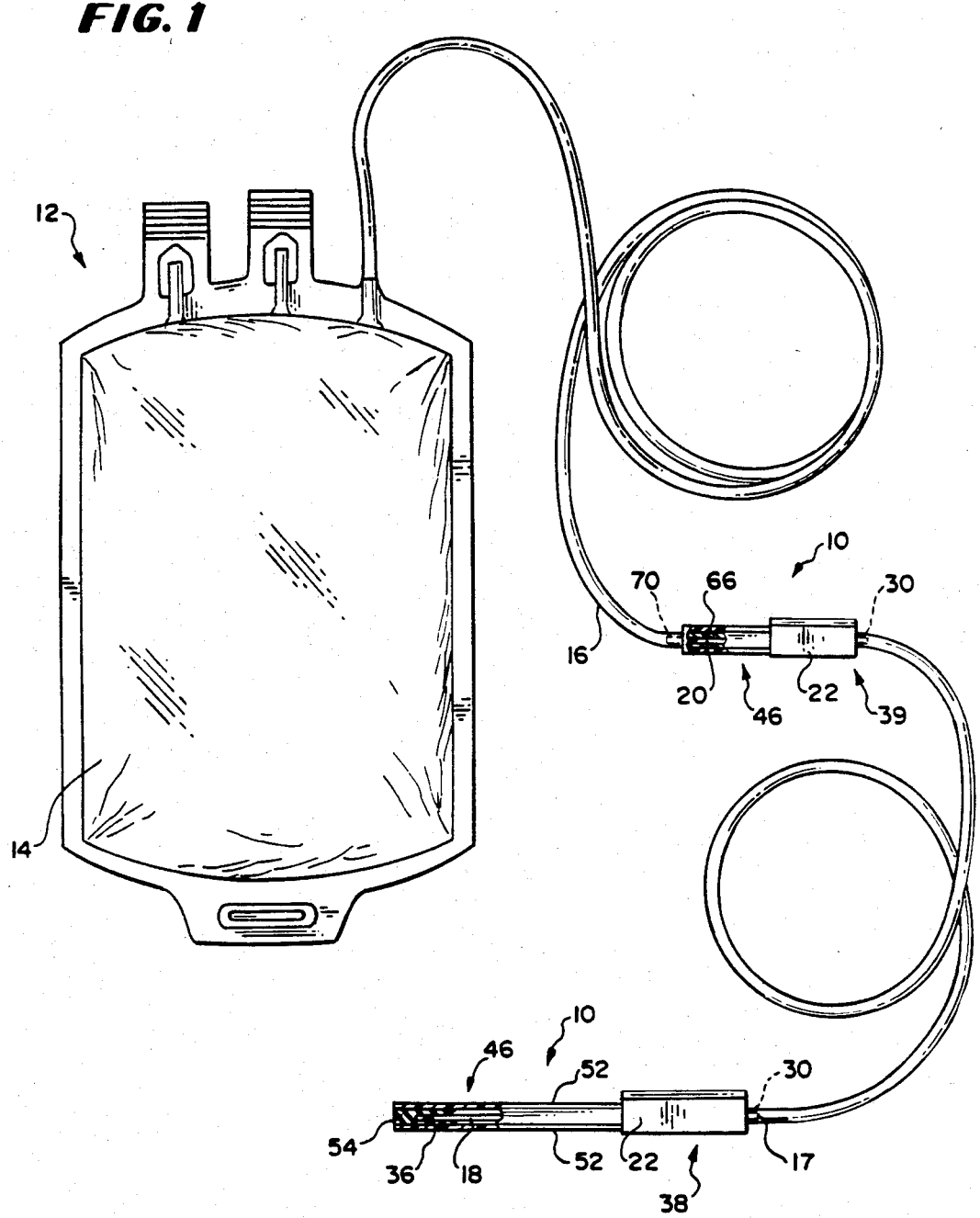

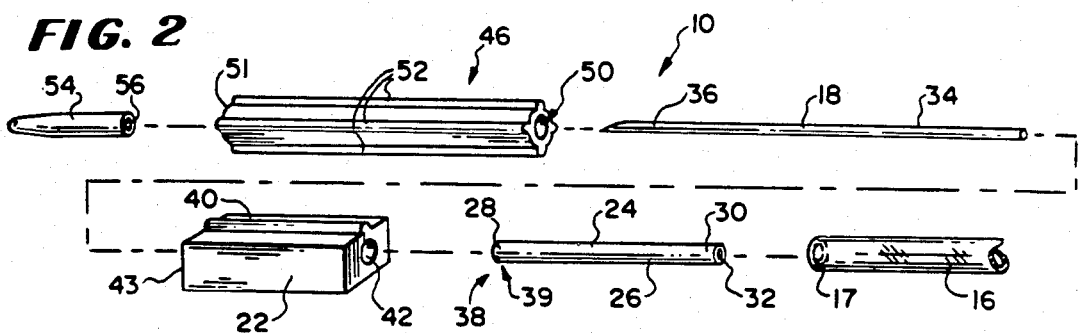
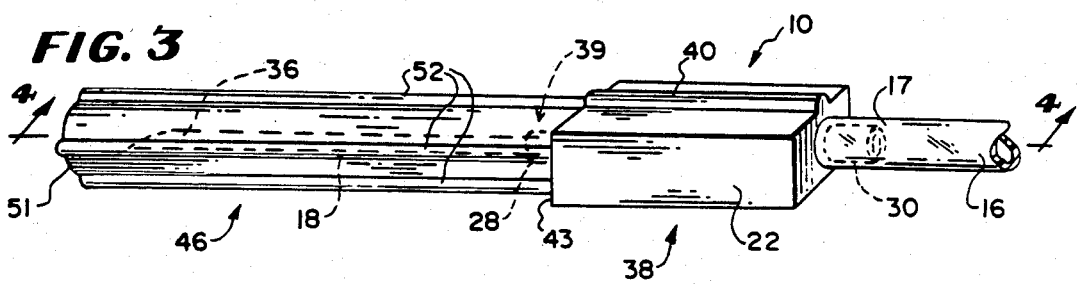
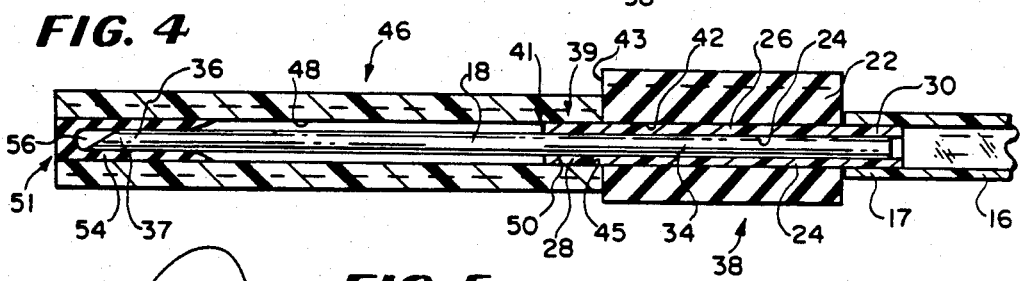
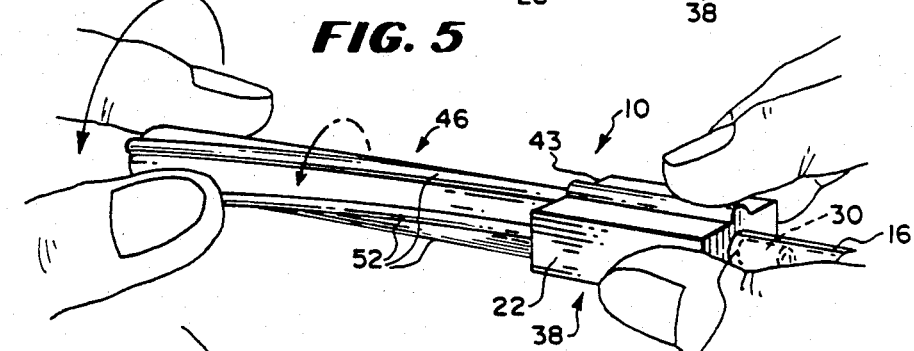
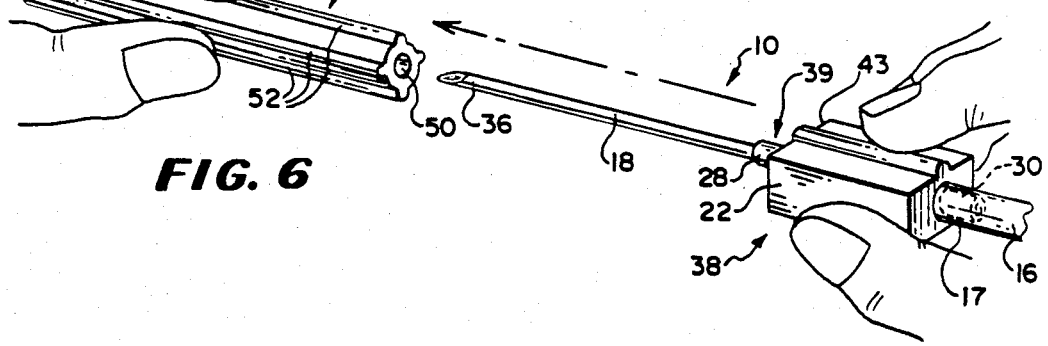

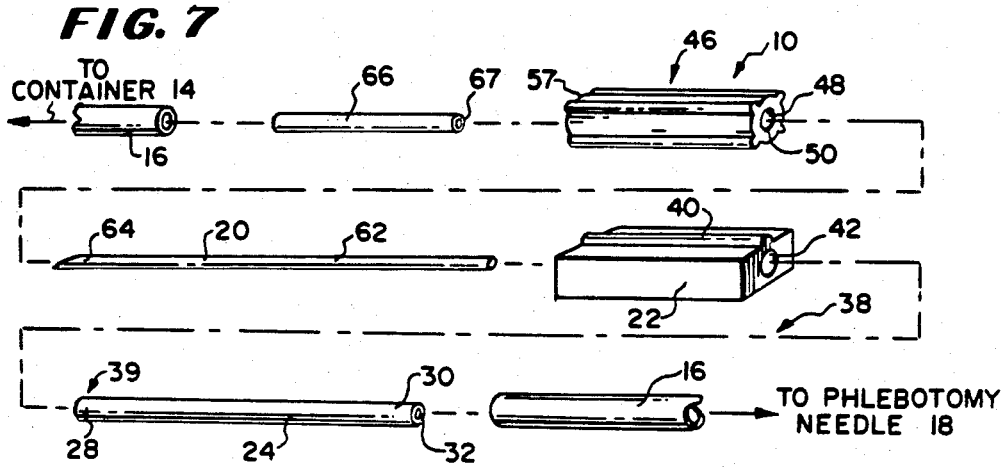
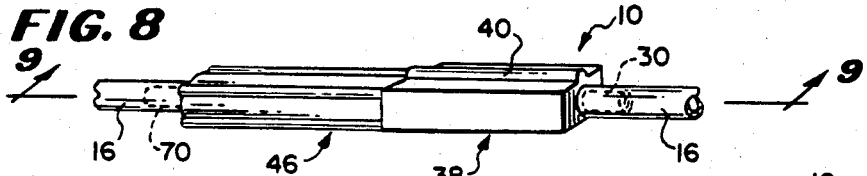
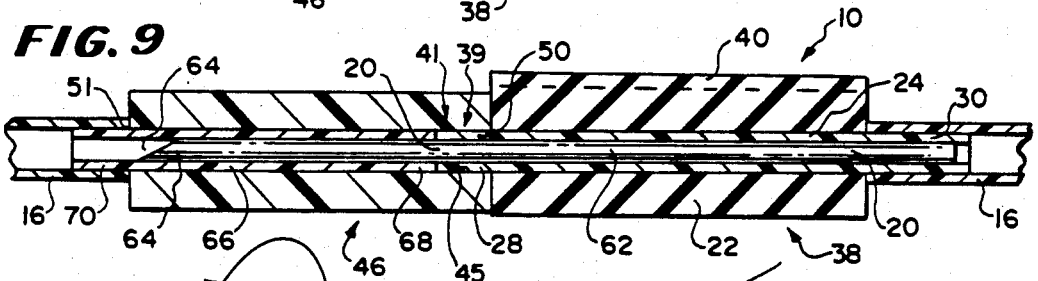
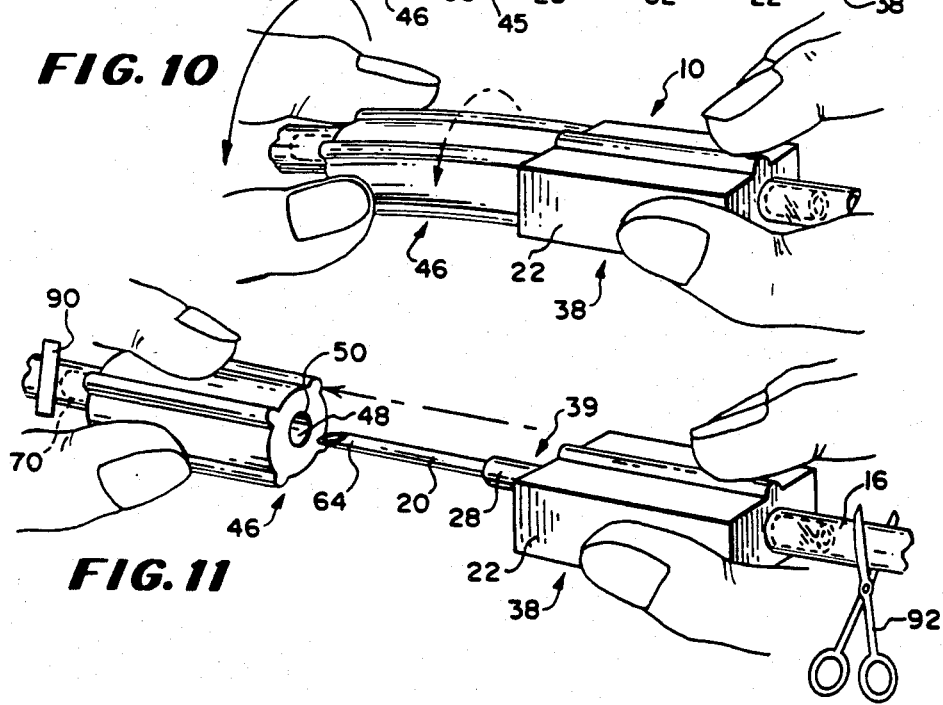
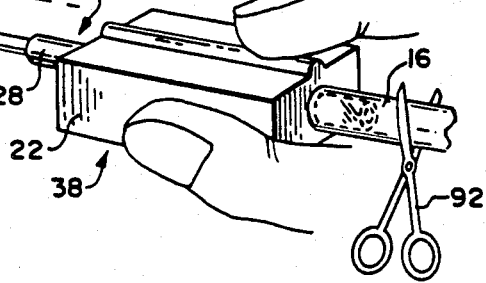

ASSEMBLY EMPLOYING A BREAKABLE THERMAL BOND WHICH IS NOT SUBSTANTIALLY EFFECTED BY PROLONGED HEAT EXPOSURE

This is a continuation of application Ser. No. 326,737, filed Dec. 2, 1981, now U.S. Pat. No. 4,402,682.

TECHNICAL FIELD OF THE INVENTION

The invention generally relates to the assembly of fabricated parts, and more particularly, to the formation of frangible connections between fabricated parts.

The invention also generally relates to cannula support assemblies, and, more particularly, to cannula support assemblies which employ cover members to enclose and protect the cannula prior to use.

DESCRIPTION OF THE PRIOR ART

Cannulas in the form of catheters, hypodermic needles, phlebotomy needles, and the like are widely used to administer and draw blood and other parenteral fluids. These cannulas are typically carried in specially designed support members, or hubs, such as those discussed in the following United States Patents:

| Gewecke | 2,712,822 | July 12, 1955 |
|---|---|---|
| McConnaughey et al | 3,096,763 | July 9, 1963 |
| Santomieri | 3,330,278 | July 11, 1967 |
| Moyer | 3,406,687 | October 22, 1968 |
| Stevens et al Re. | 28,713 | February 17, 1976 |
| Seberg | 4,192,305 | March 11, 1980 |
| Akhavi | 4,240,427 | December 23, 1980 |
| Blum | 4,266,543 | May 12, 1981 |

Cannula support members are also the subject of the following foreign documents:
British Patent Specification No. 810,860
British Patent Specification No. 840,487
Canadian Pat. No. 545,415
German Pat. No. 664,001
German Auslegeschrift No. 1,085,652
Italian Pat. No. 498,057

Cover members, or sheaths, are often provided to enclose and protect the cannulas prior to use. Cannula support assemblies having cover members or sheaths are discussed in the following United States Patents:

| Wedig | 1,100,799 | June 23, 1914 |
|---|---|---|
| Walter | 2,702,037 | February 15, 1955 |
| Melton | 2,705,008 | March 29, 1955 |
| Brookfield | 3,294,089 | December 27, 1966 |
| Pagones | 3,523,530 | August 11, 1970 |
| Geiger | 4,121,588 | October 24, 1978 |
| Oiwa | 4,180,071 | December 25, 1979 |

A cover member or sheath for a cannula is also discussed in Australian Pat. No. 159,814.

Attention is also directed to the copending patent application of Emil Soika, entitled CANNULA SUPPORT ASSEMBLY AND ASSOCIATED METHOD OF MANUFACTURE, Ser. No. 326,739, filed simultaneously with this application and assigned to the same assignee as this application.

Attention is also directed to the two copending patent applications of Edward Garver entitled SUPPORT ASSEMBLY FOR A CANNULA AND THE LIKE, Ser. No. 326,736 and AN AUTOCLAVABLE THERMOPLASTIC MATERIAL WHICH IS HEAT BONDABLE TO A CANNULA AND THE LIKE, Ser. No. 326,738, both of which also share the same filing date and assignee as this application.

It is desirable to have a cover member which protects the sterile integrity of a cannula prior to use, which can be conveniently removed to expose the cannula at the instant of use, and which can thereafter be returned to again shield the cannula, if desired. However, once such a cover member has been initially removed and returned, on purpose or by accident, it is desirable to provide some outward indication to alert potential future users that the sterile integrity of the cannula has been compromised.

It is thus one of the principal objects of this invention to provide a "tamper-proof" cannula support assembly having a cover member which, prior to its initial removal, attests to the sterile integrity of the cannula and which, after its initial removal and subsequent return, indicates that the sterile integrity of the cannula has been breached.

It is another principal object of this invention to provide a "tamper-proof" cannula support assembly having a cover member which can be easily removed at the instant of use to expose the cannula and thereafter returned to enclose the cannula.

It is yet another principal object of this invention to provide a "tamper-proof" cannula support assembly which lends itself to production on a large scale, automated basis.

SUMMARY OF THE INVENTION

To achieve these and other objects, the invention provides an assembly for supporting a cannula and the like. The assembly comprises hub means which supports the cannula with its operative end exposed beyond one end of the hub means. The hub means includes a post portion which extends outwardly from the one end of the hub means and which concentrically surrounds an adjacent section of the exposed cannula end. The assembly also includes cover means having an open end portion which fits concentrically about the post portion of the hub means. When so disposed on the post portion, the cover means encloses the operative end of the cannula. The assembly further includes means which is operatively associated with the post portion of the hub means and the open end portion of the cover means for forming therebetween a generally fluid-tight, yet severable, connection. This connection normally secures the cover means to the hub means, and thereby serves to protect the sterile integrity of the cannula. However, the connection is breakable in response to the application of a force of a predetermined magnitude upon the cover means relative to the axis of the post portion. This affords the separation of the cover means from the hub means.

In the preferred embodiment, the connection is broken by the application of a rotational force about the post portion.

By virtue of this breakable connection, the user is able to quickly and easily determine whether the sterile integrity of the cannula has been compromised prior to use simply by attempting to twist the cover means about the post portion. If such twisting is resisted, the connection between the post portion and cover means, and, with it, the sterile integrity of the cannula, is intact. If such twisting is not resisted and immediately rotates the cover means, the connection between the post portion and cover means has heretofore been broken. In this instance, the sterile integrity of the cannula is subject to doubt.

In one embodiment, the rotational force at which the connection between the cover means and the post portion breaks is significantly less than the amount of rotational force necessary to permanently rotationally deform either the post portion or the cover means. Thus, even though force is required to twist the cover means and break its connection with the post portion, both the post portion and cover means remain structurally sound to accommodate the subsequent return of the cover means to the hub means.

In one embodiment, the cover means is itself resiliently deformable about its axis in response to a rotational force which is less than that required to break the connection. Thus, when the connection between the end portion of the cover means and post portion is intact, the cover means resiliently deforms about its axis in response to the progressive application of a rotational force, until the rotational force reaches the magnitude sufficient to break the connection. This resilient deformation of the cover means, which precedes the breakage of its connection with the post portion, offers further visual and tactile assurances of the sterile integrity of the cannula prior to use. However, this resilient deformation does not adversely effect the ability to subsequently return the cover means to the hub means.

In the preferred embodiment, the breakable connection comprises a limited thermal bond which results from a purposeful matching of the materials for the post portion and the cover means, coupled with the selection of the optimal bonding area therebetween. By virtue of this preselection process, the limited thermal bond can be initially established by a period of heat exposure, after which the desired limited strength of the bond remains substantially constant, despite further heat exposure, such as autoclaving.

In one embodiment, in which the material of the post portion comprises a polyester material, the invention provides a matching material for the cover means which includes a vinyl to which silicone and, preferably, calcium carbonate have been added. In this embodiment, the rotational force necessary to break the resulting, limited bond is between approximately 10 and 14 inch ounces of torque applied about the axis of the post portion.

Other features and advantages of the embodiments of the invention will become apparent upon reviewing the following more detailed description, the drawings, and the appended claims.

DESCRIPTION OF THE DRAWINGS

FIG. 1 is a plan view, with parts broken away and in section, of a blood collection, storage, and sampling unit which includes a donor tube having a phlebotomy needle and an inline blood sampling needle, each of which is carried by a "tamper-proof" cannula support assembly which embodies various of the features of the invention;

FIG. 2 is an exploded perspective view of the "tamper-proof" cannula support assembly used in association with the phlebotomy needle shown in FIG. 1;

FIG. 3 is an assembled perspective view of the "tamper-proof" cannula support assembly shown in FIG. 2;

FIG. 4 is a section view of the "tamper-proof" cannula support assembly taken generally along line 4—4 in FIG. 3;

FIGS. 5 and 6 are perspective views showing the sequence of breaking the "tamper-proof" connection between the cover member and hub of the cannula support assembly shown in FIG. 3;

FIG. 7 is an exploded perspective view of the "tamper-proof" cannula support assembly used in association with the blood sampling needle shown in FIG. 1;

FIG. 8 is an assembled perspective view of the "tamper-proof" cannula support assembly shown in FIG. 7 in a coupled relationship;

FIG. 9 is a section view of the "tamper-proof" cannula support assembly taken generally along line 9—9 in FIG. 8;

FIGS. 10 and 11 are perspective views showing the sequence of breaking the "tamper-proof" connection between the cover member and hub of the cannula support assembly shown in FIG. 8;

Figure 12:
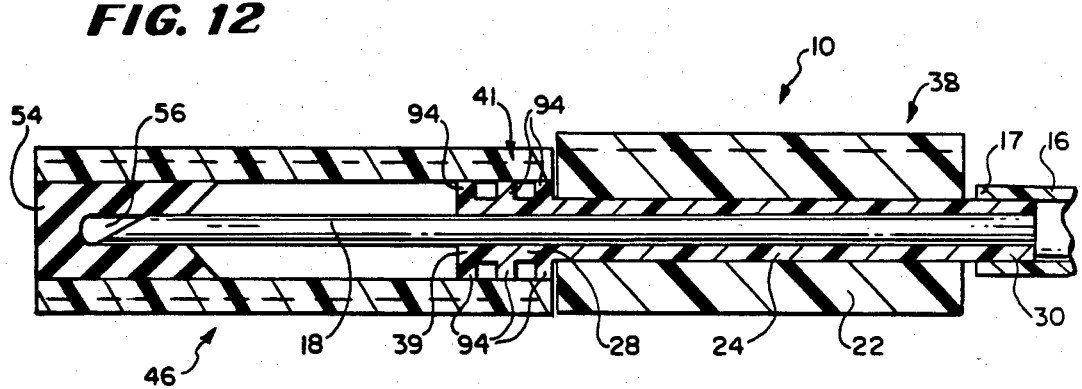
FIG. 12 is a section view of an alternate embodiment of a "tamper-proof" cannula support assembly which embodies various of the features of the invention.

Before explaining the embodiments of the invention in detail, it is to be understood that the invention is not limited in its application to the details of construction and the arrangement of components as set forth in the following description or as illustrated in the accompanying drawings. The invention is capable of other embodiments and of being practiced or carried out in various ways. Furthermore, it is to be understood that the phraseology and terminology employed herein is for the purpose of description and should not be regarded as limiting.

DESCRIPTION OF THE PREFERRED EMBODIMENTS

A "tamper-proof" cannula support assembly 10 is shown in the drawings. The term "cannula" is used herein to broadly signify a small tube which is insertable into a body cavity, duct, or vessel. Examples of cannulas include catheters, hypodermic needles, and phlebotomy needles.

The assembly 10 which will be described herein is applicable for use in a diverse number of environments and in conjunction with catheters, hypodermic needles, and various other needle arrangements used to direct and channel blood, parenteral fluids, and medicines to and from the body. The assembly 10 is particularly well suited for interconnecting a cannula body with flexible tubing. For this reason, the illustrated embodiments envision this specific use.

Reference is first made to FIG. 1, in which a representative blood collection, storage, and sampling unit 12 is shown. While various constructions are possible, in the illustrated embodiment, the unit 12 includes a blood collection container 14, which typically is a flexible bag made of medical grade polyvinyl chloride plastic material. A donor tube 16, which typically is also made of a flexible medical grade polyvinyl chloride plastic material, is integrally attached to and carried by the container 14. A cannula body in the form of a phlebotomy needle 18 is attached in flow communication with the outer end 17 of the donor tube 16. The needle 18 serves after venipuncture to channel blood from a patient or donor through the donor tube 16 and into the container 14.

Another cannula body in the form of a blood sampling needle 20 is attached in line with the donor tube 16 upstream of the phlebotomy needle 18. The sampling needle 20 enables an attendant to obtain blood samples for laboratory purposes and testing after completion of the blood collection procedure.

In this specific operative environment, one embodiment of the "tamper-proof" cannula support assembly 10 is utilized to support the phlebotomy needle 18 and to attach the needle 18 to the end 17 of the donor tube 16. This embodiment of the support assembly 10 is shown in more detail in FIGS. 2 through 6.

Another embodiment of the "tamper-proof" cannula support assembly 10 is utilized to support the sampling needle 20 and to attach the needle 20 inline with the donor tube 16. This embodiment of the support assembly 10 is shown in more detail in FIGS. 7 through 11.

Figure 13:
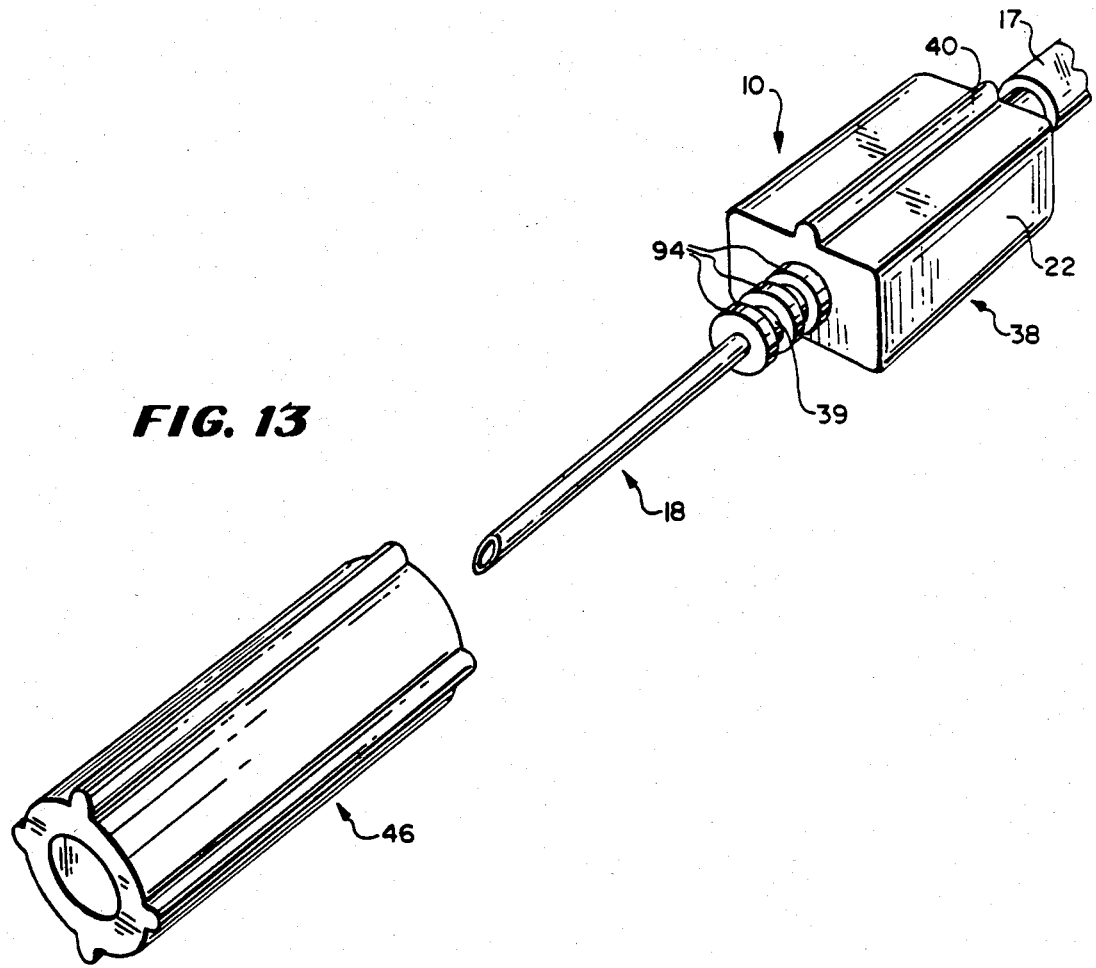
FIG. 13 is a perspective view of the cannula support assembly shown in FIG. 12 after the "tamper-proof" connection has been broken.

An alternate embodiment of a "tamper-proof" cannula support assembly 10 which embodies various of the features of the invention and which is applicable for use in association with either the phlebotomy needle 18 or sampling needle 20 is shown in FIGS. 12 and 13.

Reference is first made to FIGS. 2 through 6 and to the embodiment of the assembly 10 utilized to support the phlebotomy needle 18. In this embodiment, the assembly 10 includes hub means 38 which is compact and easily handled and manipulated between the fingertips of the attendant (see, in particular, FIGS. 5 and 6). The hub means 38 supports the phlebotomy needle 18 with its operative, or beveled, end 36 extending axially beyond one end 43 of the hub means 38.

The hub means 38 includes a post portion 39 (as best shown in FIGS. 4 and 6) which projects outwardly from the one end 43 of the hub means 38 and concentrically encircles an adjacent section of the operative end 36 of the needle 18.

While the hub means 38 may be variously constructed, in the illustrated embodiment, the hub means 38 is constructed along the lines disclosed in the heretofore cited copending U.S. patent application of Emil Soika, entitled CANNULA SUPPORT ASSEMBLY AND ITS METHOD OF MANUFACTURE.

More particularly, the hub means 38 comprises a first member 22 and a second member 24. The first and second members 22 and 24 each take an elongated, tubular form having an essentially uniform cross-sectional shape. As pointed out in the above-cited Soika patent application, this construction enables the manufacture of the first and second members 22 and 24 utilizing known ram or screw extrusion techniques. It should be appreciated, however, that the hub means 38 and its associated post portion 39 could also be formed as a single piece injection or compression molded unit.

As is best shown in FIG. 4, the second member 24 has a main body portion 26, which is carried within a bore 42 (see FIG. 1) formed in the first member 22, and opposite end portions, respectively 28 and 30, each of which is disposed outwardly of the first member 22.

The second member 24 also has a bore 32 in which the shank 34 of the phlebotomy needle 18 (see FIG. 4) is secured. The shank 34 can be secured within the second member bore 32 by various means, such as by use of adhesive or epoxy bonding (as disclosed in the just referenced copending patent application of Emil Soika), or by thermal bonding, as disclosed in the heretofore cited copending U.S. patent applications of Edward Garver, entitled SUPPORT ASSEMBLY FOR A CANNULA AND THE LIKE AND ITS METHOD OF MANUFACTURE and AN AUTOCLAVABLE THERMOPLASTIC MATERIAL WHICH IS HEAT BONDABLE TO A CANNULA AND THE LIKE.

By virtue of this construction, the operative end 36 of the needle 18 supported in an outwardly projecting, exposed position beyond the second member end portion which is adjacent to the end 43 of the hub means 38. In the illustrated embodiment, this is second member end portion 28. This end portion 28 thus corresponds with the heretofore described post portion 39 of the hub means 38.

The other outwardly disposed end 30 of the second member 24 readily accommodates attachment of the hub assembly 38 to the end 17 of the donor tube 16.

The first member 22 preferably includes an outwardly projecting ridge or shoulder 40 which extends along one exterior surface axially of the first member bore 42. This ridge 40 serves as a reference point for the proper alignment of the beveled end 36 of the needle 18 relative to the hub means 38 during the assembly process. Proper bevel orientation is desirable, because it assures that the sharpest part of the needle 18 breaks the skin during venipuncture.

In addition to facilitating the initial alignment of the beveled end 36 of the needle 18 during the assembly process, the ridge 40 functions as a visual and tactile guide in the hands of the attendant (see FIG. 6) to assist him or her in positioning the beveled end 36 during venipuncture.

The assembly 10 further includes cover means 46 which protects the sterile integrity of the phlebotomy needle 18 prior to venipuncture and which seals the needle 18 against fluid loss prior to and after use.

As can best be seen in FIGS. 4 and 6, the cover means 46 has an open end portion 50 which fits concentrically about the post portion 39 (i.e., second member end 28) of the hub means 38. The cover means 46 further includes and an open interior 48 which extends from the end portion 50 and serves to enclose the operative portion 36 of the needle 18.

The cover means 46, like the hub means 38, may be variously constructed. However, in the illustrated embodiment, the cover means 46, like the hub means 38, is constructed along the lines disclosed in the above-cited Soika patent application.

More particularly, the cover means 46 takes an elongated, tubular form (see FIGS. 2 and 4) having an essentially uniform cross-sectional shape with oppositely spaced ends 50 and 51, between which the open interior 48 of the cover means 46 extends. As with the construction of the first and second members 22 and 24, this elongated, tubular, and generally uniform configuration enables the manufacture of the cover means 46 utilizing known ram or screw extrusion processes. However, as with the hub means 38, it should be appreciated that the cover means 46 could also be formed as an injection or compression molded piece.

Axially extending and uniformly radially spaced ridges 52 are formed on the exterior of the cover means 46 of the illustrated embodiment to facilitate the gripping and manipulation of the cover means 46 by the attendant (see FIGS. 5 and 6).

As can be seen in FIG. 4, the interior diameter of the open interior 48 of the cover means 46 preferably exceeds the exterior diameter of the exposed portion 36 of the phlebotomy needle 18. Thus, when the cover means 46 is disposed on the hub means 38, the open interior 48 is spaced radially outwardly of, and thus disposed in a non-contiguous relationship with, the needle 18 along its entire outwardly disposed length.

In order to affect a fluid-tight seal with the needle 18 within the confines of the open interior 48 of the cover means 46, the cover means 46 of the illustrated embodiment includes a member 54, which is preferably formed of a resiliently compressible material, such as compression molded rubber. The member 54 is insertable in a press-fit relationship through the outermost disposed open end 51 of the cover means 44 to occupy only the outermost portion of the open interior 48 (see FIG. 4).

As can be seen in FIG. 4, the member 54 includes a chamber or pocket 56 which is configured to sealingly envelop the outermost tip 37 of the beveled end 36 of the needle 18 when the hub and cover means 38 and 46 are coupled together. The pocket 56 thereby seals the needle tip 37 from communication with the remainder of the open interior 48 of the cover means 46 and provides a positive fluid shut-off for the needle 18 within the open interior 48.

Because only the outermost tip 37 of the needle 18 is in sealing contact with the pocket 56 of the member 54, there is a minimum of friction, or drag, created between the needle 18 and the cover means 46 during removal of the cover means 46 to expose the needle 18. Such removal thus does not tend to draw or suck fluid out of the needle 18. By the same token, return of the cover means 46 onto the hub means 38 is achieved with a minimum of effort.

Recognizing also that it is desirable to coat the exterior of the phlebotomy needle 18 with silicone to facilitate a more comfortable venipuncture, the very limited intimate contact between the needle 18 and the cover means 46 shown in FIGS. 2 through 6 further serves to protect the silicone coating along most of the outwardly exposed portion 36 of the needle 18 against friction loss during removal or return of the cover means 46. This construction thus also ultimately contributes to a more comfortable venipuncture.

From the foregoing, it can be seen that the cover means 46 serves to protect the sterile integrity of the needle 18 prior to use, but can be easily removed and returned to the post portion 39 of the hub means 38 when desired.

In order to provide positive assurance that the cover means 46 has not been tampered with in a manner which compromises the sterile integrity of the needle 18, the assembly 10 includes means 41 operatively associated with the post portion 39 of the hub means 38 and the end portion 50 of the cover means 46 for forming therebetween a generally fluid-tight connection. The connecting means 41 normally secures the cover means 46 to the hub means 38 (see FIGS. 3 and 4) and prevents either rotational or lateral movement of the end portion 50 relative to the post portion 39.

The connecting means 41 provided by the invention is breakable only in response to the deliberate application of a force of a predetermined magnitude upon the cover means 46 relative to the axis of the post portion 39. Only by so breaking the connecting means 41 is the user able to initially separate the cover means 46 from the hub means 38.

In the preferred and illustrated embodiments, the force which serves to break the connecting means 41 is applied rotationally about the post portion 39 by twisting the cover means 46.

In accordance with the invention, the magnitude of the rotational force necessary to break the connecting means 41 is more than a nominal amount of force, such as that which would be provided by a mere interference fit between the members. Thus, the chance of accidentally breaking the connecting means 41 during handling is minimized.

However, also in accordance with the invention, the force required is not large enough to permanently rotationally deform either the cover means 46 or the post portion 39 of the hub means 38. Thus, as can be seen in FIG. 6, after the connecting means 41 has been broken, both the post portion 39 and cover means 46 remain physically intact and structurally unaltered to permit a subsequent rejoining of the open end portion 50 of the cover means 46 about the post portion 39.

Preferably, the cover means 46 is resiliently deformable about its axis in response to a rotational force which is less than the rotational force at which the connecting means 41 breaks. As will be described in greater detail later herein, this provides further visual and tactile assurance of the integrity of the connecting means 41 prior to the time it is broken.

However, and further in accordance with the invention, after the connecting means 41 has been initially broken, any subsequent return or removal of the cover means 46 from the hub means 38 can be accomplished with relative ease. Thus, there can be no question that the connecting means 41 has been broken and the sterile integrity of the needle 18 has been breached.

The connecting means 41 which enables this selectively breakable connection between the end portion 50 and the post portion 39 may vary. In the preferred embodiment, the means 41 takes the form of a limited, or yieldable, thermal bond 45 (see FIG. 4) which is formed along the concentric interface of the open end portion 50 about the post portion 39. This limited thermal bond 45 purposefully arises from the careful matching of the material utilized for the cover means 46 to the material utilized for the post portion 50, coupled with the careful choice of the optimal bonding area therebetween.

More particularly, dominating the selection of all the materials for the hub and cover means 38 and 46 of the assembly 10 is the desirability that the assembly 10 be made of materials suitable for contact with human blood. It is also highly preferred that the entire assembly 10 be autoclavable.

With regard to the hub means 38, a vinyl material is well suited for use as the first member 22.

With regard to the material of the post portion 39 (which, in the illustrated embodiment, constitutes the end 28 of the second member 24) additional selection preferences arise. For example, it is desirable that the material of the entire second member 24 be solvent bondable to the medical grade polyvinyl chloride tubing 16 to facilitate its attachment thereto, as well as be thermally bondable to the needle 18 in a manner which minimizes the chance of air gaps or voids in the bond through which blood and parenteral fluids can leak.

As discussed in the previously cited copending applications of Edward Garver, the second member 24 (and thus its end 28 constituting the post portion 39) is preferably fabricated from a polyester material comprising approximately 60% by weight of a thermoplastic polyetherester manufactured and sold by E. I. Du Pont as HYTREL 4056 and approximately 40% by weight of a poly(ethylene terephthalate)-based copolymer manufactured and sold by Eastman Chemical Products, Inc. as KODAR ™ PETG Copolyester 6763. This polyester material is autoclavable and exhibits superior bonding characteristics to the needle 18.

The selection of a polyester material for the post portion 39 to enable superior bonding characteristics to the needle 18, in turn, complicates the selection of materials for the cover means 46 to achieve the limited thermal bond 45 desired.

For example, polypropylene materials, which are approved for blood contact and are autoclavable, are nevertheless unacceptable for use as the cover means 46. This is because polypropylene materials are chemically dissimilar to the polyester material of the post portion 39. As a result, it is not possible to affect any bond, thermal or otherwise, between the two materials, much less the desired limited bond 45.

Furthermore, the use of a plasticized polyvinyl chloride material, a known and widely used autoclavable material suited to blood contact, is also unacceptable. While vinyl is heat bondable to the polyester material of the post portion 39, the strength of the bond progressively increases as the heat history, or exposure, of the vinyl increases, reaching magnitudes well in excess of the torque resistance strength of the polyester post portion 39 (approximately 20 inch ounces).

Referring to Example I in the following Table, it can be seen that, after being exposed to autoclaving (temperatures between approximately 230° F. and 250° F.), it is necessary to apply a "take-off" torque consistently in excess of 22 inch ounces about the axis of the post portion 39 in order to break the thermal bond between the open end portion 50 of a vinyl cover means 46 and the polyester post portion 39. Rotational deformation of the post portion 39 results.

Referring now to Example II in the following Table, it was found that the addition of calcium carbonate to the vinyl did not significantly reduce the take-off torque below the torque resistance strength of the polyester post 39. The resulting take-off torques were observed to widely vary between 19 and 26 inch ounces.

However, as can be seen in Example III of the following Table, it was discovered that the addition of a small amount (approximately 3% by weight) of silicone (Dow Corning 200, 12,500 Cs) to the vinyl did result in a significant reduction in the strength of the thermal bond and provided a defined range of take-off torques, the greatest of which (17 inch ounces) was below the torque resistance strength of the polyester post portion 39.

As can be seen in Example IV of the following Table, it was further discovered that the addition of calcium carbonate to the vinyl-silicone mixture further reduced the maximum take-off torque observed. The addition of calcium carbonate also led to a relatively more narrowly defined range of take-off torques than that associated with the vinyl-silicone mixture alone. A more uniform finished product can thus result.

For example, sixty (60) cover means 46 were fabricated utilizing the composition of Example V in the following Table. After batch sterilization, all but six of the cover means 46 so constructed had a take-off torque which lay in the narrowly defined range of between 9 and 14 inch ounces. The maximum take-off torque experienced (one unit) was 16 inch ounces. The minimum take-off torque experienced (two units) was 8 inch ounces.

The effect of the calcium carbonate leading to a more narrowly defined range of take-off torques is surprising in light of Example II heretofore discussed.

TABLE

| Materials | Percent by Weight | Take-off Torque (after autoclaving) |
|---|---|---|
| Example I | | |
| Vinyl | 100% | Consistently in excess of 22 inch ounces |
| Example II | | |
| Vinyl | 75% | approximately 19 to 26 inch ounces |
| Calcium Carbonate | 25% | |
| Example III | | |
| Vinyl | 97.09% | approximately 10 to 17 inch ounces |
| Silicone | 2.91% | |
| Example IV | | |
| Vinyl | 72.09% | approximately 10 to 14 inch ounces |
| Calcium Carbonate | 25.00% | |
| Silicone | 2.91% | |
| Example V | | |
| Vinyl | 77.00% | approximately 9 to 14 inch ounces |
| Calcium Carbonate | 19.90% | |
| Silicone | 3.1% | |

The percent by weight of the vinyl in the above Table includes a polyvinyl chloride resin, a plasticizer (such as di-2-ethylhexyl phthalate), and suitable heat stabilizers (such as epoxidized vegetable oils and metal soaps).

The take-off torque is measured about the axis of the polyester post portion 39 as the cover means 46 is rotated relative thereto.

Take-off torques which lie within the ranges associated with Examples III, IV, and V require a deliberate application of force, and are thus not susceptible of being inadvertently or accidentally developed. Nevertheless, the deliberate application of force needed to generate take-off torques within this defined range is well within the physical capabilities of the average user without undue effort or fatigue. The more narrowly defined ranges of take-off torques associated with Examples IV and V are preferred, because they enable a more uniform finished product.

In order to uniformly achieve the relatively narrowly defined range of take-off torques associated with Examples IV and V, it was determined that the surface area of the interface between the open end portion 50 and post portion 39, along which the thermal bond 45 is formed, is preferably between approximately 0.04 square inches and approximately 0.06 square inches.

Furthermore, in order to uniformly achieve the relatively narrowly defined range of take-off torques associated with Examples IV and V, it was determined that a heat exposure cycle of approximately 250° F. for approximately 30 minutes is preferred.

After this heat exposure cycle, the hub means 38 and attached cover means 46 can be handled and batch sterilized and pasteurized as a finished assembly 10, as shown in FIG. 3. The desired limited strength of the thermal bond between the cover means 46 and the post portion 39 (as measured in terms of the take-off torques expressed in the Table) does not significantly increase during the additional heat exposure occasioned by autoclaving and pasteurization.

While the particular ranges of take-off torques associated with Examples IV and V can vary in absolute terms from those found in the Table according to the surface area of the bond 45 and the specific heat sterilization cycle utilized, they nevertheless have been observed to consistently remain below levels at which rotational deformation of the post portion 39 occurs. The bond 45 thus lends itself to mass production, automated manufacturing techniques.

By virtue of the limited thermal bond 45 as heretofore described, the assembly 10 is indeed "tamper-proof". As shown in FIGS. 5 and 6, in order to initially remove the cover means 46, it is necessary to deliberately twist the cover assembly 46 relative to the hub means 38 until the requisite take-off torque is reached. It should be appreciated that the bond 45 could also be broken by laterally pulling on the cover means 46, but the effort involved in this technique would far exceed that associated with twisting.

Furthermore, the materials of Examples III, IV and V in the above Table are each semi-rigid and resiliently deformable in response to torques less than the requisite take-off torque. Thus, the presence of the bond 45, which normally serves to resist the twisting of the cover means 46 about the post portion 39, causes the cover means 46 to resiliently twist or deform about itself (see FIG. 5) before enough torque is developed to break the bond 45. This resilient twisting of the cover means 46 does not permanently deform the cover means 46. The user is thus able to quickly test the presence of the bond 45, and thus the sterile integrity of the needle 18, by observing whether or not it is possible to initially resiliently twist or deform the cover means 46 about itself, without effecting the subsequent ability to rejoin the cover means 46 about the post portion 39.

It has been further observed that the breakage of the bond 45 between the polyester material of the post portion 39 and the vinyl-silicone-calcium carbonate material of the cover means 46 (Examples IV and V) is accompanied by an audible "snapping" sound.

By virtue of the invention, if the cover means 46 can be removed from the hub means 38 without resilient deformation and/or without an audible "snapping" sound, this serves as a clear indication that the thermal bond 45 has in all likelihood been previously broken. The cover means 46 has thus probably been previously been removed and returned. The sterile integrity of the needle 18 is subject to question.

It has been further observed that the material of Examples IV and V relaxes in the presence of heat. By virtue of this desirable characteristic, the end portion 50 of the cover means 46 can be normally dimensioned for a tight interference fit upon the post portion 39. This fit temporarily secures the cover means 46 to the post portion 39 during the manufacturing process. This fit also provides intimate contact along the bonding area to facilitate the formation of a hermetic thermal bond. However, during heat exposure and the formation of the thermal bond 45, the end portion 50 of the cover means 46 relaxes and conforms to the exterior dimension of the post portion 39.

Thus, after the thermal bond 45 is broken, the end portion 50 of the cover means 46 is virtually free spinning about the post portion 39.

This free spinning fit greatly facilitates the removal of the cover means 46 at time of venipuncture and the subsequent return of the cover means 46 upon the post portion 39, if desired. It also serves as a further outward indication that the bond 45 has been broken.

The same "tamper-proof" bond 45 as just described in context of the assembly 10 for the phlebotomy needle 18 is readily adaptable for similarly "tamper-proofing" the embodiment of the cannula support assembly 10 which is associated with the sampling needle 20 and which is shown in FIGS. 7 through 11.

This embodiment is similar in many respects to the support assembly embodiment associated with the phlebotomy needle 18. For this reason, common structural elements are assigned common reference numerals.

The assembly 10 shown in FIGS. 7 through 11 includes the heretofore described hub means 38 and cover means 46.

As in the embodiment shown in FIGS. 2 through 6, the hub means 38 includes first and second members, respectively 22 and 24, each having a bore, respectively 42 and 32. Also like the first described hub means 38, the second member 24 is disposed within the first member bore 42, with its end portions 28 and 30 each projecting outwardly from the first member 22 (see FIG. 9).

The second member bore 32 of the second embodiment accommodates the shank 62 of the sampling needle 20, just as the shank 34 of the phlebotomy needle 18 of the first embodiment is accommodated in its associated second member bore 32 (see FIG. 9). The beveled end 64 of the sampling needle 20 is thereby supported in the same outwardly projecting exposed position beyond the second member end 28 (see FIG. 11), which also constitutes the post portion 39 of the hub means 38. The sampling needle 20 is properly aligned relative to the orientation shoulder 40.

The cover means 46 of the FIGS. 7 through 11 embodiment, like the cover means 46 of the first embodiment, includes an open interior 48 to accommodate the exposed portion 64 of the sampling needle 20. Also like the first described cover means 46, the cover means 46 has an open end 50 which fits concentrically about the outwardly disposed second member end portion 28 (or post portion 39) from which the sampling needle 20 extends (see FIG. 9).

However, unlike the first described cover means 46, which utilizes the member 54 to plug the opposite end 51 of the cover means 46 and seal the needle tip 37, the cover means 46 of this embodiment (see FIG. 9) includes a tubular member 66 having a bore 67 which accommodates the beveled end 64 of the sampling needle 20. The tubular member 66 has one end 68 which is disposed in an interference fit within a portion of the open interior 48 to receive the beveled needle end 64. An opposite end 70 of the tubular member 66 extends outwardly from the end 51 of the cover means 46 for attachment to the donor tube 16 downstream of the container 14. Another portion of the donor tube 16 is likewise attached to the outwardly extending end 30 of the second member 24 upstream of the phlebotomy needle 18 (see FIG. 1).

As is shown in FIG. 10, when coupled together, the hub means 38 and the cover means 46 afford the flow of fluid through the sampling needle 20 between the phlebotomy needle 18 and the container 14.

By purposefully matching the materials for the post portion 39 and cover means 46 in the manner heretofore described, and by subjecting the assembly 10 to the same heat treatment as heretofore described, the same limited thermal bond 45 can also be formed to normally secure the hub and cover means 38 and 46 together.

By virtue of this bond 45, the cover means 46 may be separated from the hub means 38, when desired, only by twisting the cover means 46 about the post portion 39 to develop the requisite take-off torque (see FIG. 10). The cover means 46 can then be separated (see FIG. 11) from the hub means 38 to interrupt the fluid flow between the phlebotomy needle 18 and the container 14 and to afford the drawing of fluid samples through the needle 20.

In the context of the illustrated use, the hub and cover means 38 and 46 are typically separated after a unit of blood has been collected in the container 14. Prior to separation, the donor tube 16 should be first permanently sealed downstream of the cover means 46 such as by use of a hand sealer clip 90 or the like (see FIG. 11). The donor tube 16 should also be temporarily clamped at this time, such as by use of a hemostat 92 or the like, upstream of the hub means 38.

Separation of the hub and cover means 38 and 46 can proceed, as shown sequentially in FIGS. 10 and 11. By selectively releasing the hemostat 92, one or more blood samples of the collected blood may be obtained through the blood sampling needle 20 for laboratory tests and the like utilizing the pre-existing phlebotomy.

From the foregoing, it should be appreciated that the connecting means 41 as heretofore described is broadly applicable for use in diverse situations whenever it is desired to removably secure one member (corresponding to the cover means 46) about an associated post member (corresponding to the post portion 39 of the hub means 38).

It should also be appreciated that the connecting means 41 can utilize various alternative constructions, other than the thermal bond 45 heretofore described, for achieving the same yieldable connection between the two members.

For example, one such alternative embodiment of the connecting means 41 is shown in FIGS. 12 and 13. In this embodiment, the surface area of the periphery of the post portion 39 of the hub means 38 is reduced by the provision of a series of axially spaced, outwardly radially extending ribs 94. The open end portion 50 of the cover means fits concentrically about the radial ribs 94.

The ribs 94 decrease the surface area of the interface between the open end portion 50 and the post portion 39, and thereby serve to lessen the strength of any bond therebetween. Then the end portion 50 can be joined to the ribs 94, such as by thermal bonding or by solvent bonding, to removably secure the cover means 46 to the hub means 38.

In this embodiment, the desired take-off torque necessary to break the limited bond can be controlled by the number and size of the ribs 94 as well as by the selection of materials, to meet the desired performance objectives. Utilizing this approach, and compatible materials which permit solvent and/or thermal bonding may be utilized.

Another example (not shown) of an alternative means to effect a breakable connection is to utilize a polyolefin material for the cover means 46 whose interior surface has been treated, such as by flame treatment, corona discharge, or plasma treating, to increase the surface energy of the polyolefin to enable adhesive bonding to the polyester post 39. By controlling the proper surface treatment, a comparable limited bond can be achieved.

Yet another example (not shown) of an alternative means is to coextrude the cover means 46 to include an inner surface of a first material which bonds to the material of the post portion 39, and a concentric outer surface of a second material which bonds to the first material, but with less bonding strength than the bond between the first material and the post portion 39. When the post portion 39 is a polyester material, an ethyl vinyl acetate (EVA) can serve as the inner surface material and a vinyl material can serve as the outer surface material. Because a bond formed between the EVA and the polyester post portion 39 will be stronger than the bond between the EVA and the adjacent vinyl, twisting the cover means 46 about the post portion 39 will cause the EVA-vinyl bond to break before the EVA-polyester bond. Separation of the cover means 46 can be effected without deformation to the post portion 39.

As in the other illustrated and described embodiments, the magnitude of the take-off torque (i.e., the torque necessary to break the EVA-vinyl bond prior to the EVA-polyester bond) can be controlled by the proper preselection of materials.

In all of the above alternate embodiments, as with the thermal bond 45 in the FIGS. 2 through 11 embodiments, the tamper-proof connection between the cover means 46 and hub means 38 is hermetic in nature, and thus serves to preserve the sterile integrity of the needle 18 or 20 prior to use; is purposefully limited in strength and is not effected by subsequent heat exposure, thus tolerating autoclaving and pasteurization; provides a take-off torque below that at which deformation of the post portion 39 occurs, thus preserving the structural integrity of the post portion 39 for subsequent rejoining of the cover means 46; and permits the user to quickly and easily determine whether the sterile integrity of the cannula has been compromised prior to venipuncture.

Various of the features of the invention are set forth in the following claims.

We claim:

1. An assembly comprising two members which are releasably secured together by a thermal bond which is selectively breakable in response to the application of a force which does not cause permanent deformation of either member, regardless or prolonged exposure of said assembly to heat, the composition of one of said members comprising an autoclavable polyester material, and the composition of the other one of said members consisting essentially of between approximately 72% and 77% by weight of a vinyl material, approximately 3% by weight of a silicone material, and the remainder comprising calcium carbonate.

* * * * *